United States Patent [19]
Blades et al.

[11] Patent Number: 6,111,408
[45] Date of Patent: Aug. 29, 2000

[54] NUCLEAR MAGNETIC RESONANCE SENSING APPARATUS AND TECHNIQUES FOR DOWNHOLE MEASUREMENTS

[75] Inventors: Thomas Blades, Kingwood, Tex.; Manfred Prammer, Downingtown, Pa.

[73] Assignee: Numar Corporation, Malvern, Pa.

[21] Appl. No.: 08/996,716

[22] Filed: Dec. 23, 1997

[51] Int. Cl.[7] .................................................. G01V 3/00
[52] U.S. Cl. ........................................ 324/303; 324/307
[58] Field of Search .................................. 324/303, 307

[56] References Cited

U.S. PATENT DOCUMENTS

| Re. 32,913 | 4/1989 | Clark ........................................ 324/338 |
| 1,158,959 | 11/1915 | Beach . |
| 2,912,641 | 7/1959 | Ruble ...................................... 324/303 |
| 2,973,471 | 2/1961 | Armistead et al. ...................... 324/303 |

(List continued on next page.)

FOREIGN PATENT DOCUMENTS

| 0 581 666 A3 | 2/1994 | European Pat. Off. ......... G01V 3/32 |
| 0 649 035 B1 | 4/1995 | European Pat. Off. ......... G01V 3/32 |

OTHER PUBLICATIONS

International Publication No. WO 98/25164, Publication Date Jun. 11, 1998; from International Application No. PCT/US97/21889, Filed Nov. 26, 1997; Priority Data: Serial No. 08/759,829, Filed Dec. 4, 1996.

Morriss et al., "Hydrocarbon Saturation and Viscosity Estimation for NMR Logging in the Belridge Diatomite," 35th SPWLA Anual Logging Symposium (Jun. 19–22, 1994), pp. 1–24.

Carr et al., "Effects of Diffusion on Free Precision in Nuclear Magnetic Resonance Experiments," *Physical Review*, vol. 94, No. 3 (May 1, 1954), pp. 630–638.

Schlumberger Wireline & Testing, "Combinable Magnetic Resonance tool reliably indicates water–free production and reveals hard–to–find pay zones," (Jun. 1995).

Morriss et al., "Field Test of an Experimental Pulsed Nuclear Magnetism Tool," SPWLA Annual Logging Symposium (Jun. 13–16, 1993), pp. 1–23.

Coates et al., "Core Data and the MRL Show—A New Approach to 'Formation Factor," National SPWLA Convention (Jun. 15, 1992), pp. 1–15.

Kleinberg et al., "Novel NMR Apparatus for Investigating an External Sample," *Journal of Magnetic Resonance*, (1992) pp. 466–485.

Coates et al., "An Investigation of a New Magnetic Resonance Imaging Log," National SPWLA Convention (Jun. 18, 1991), pp. 1–24.

Howard et al., "Proton Magnetic Resonance and Pore–Size Variations in Reservoir Sandstones," *Society of Petroleum Engineers* (1990), pp. 733–741.

(List continued on next page.)

*Primary Examiner*—Christine K. Oda
*Assistant Examiner*—Tiffany A. Fetzner
*Attorney, Agent, or Firm*—Pennie & Edmonds LLP

[57] ABSTRACT

A method and apparatus are disclosed for using nuclear magnetic resonance (NMR) techniques to obtain information relating to fluids present near geologic structures. A modular NMR tester which can be located within a standard modular logging tool is used for direct downhole NMR measurements of various parameters of fluid samples of geologic formations near the walls of a borehole. The tester has a vessel made of a non-conductive material and a surrounding permanent magnet that creates a uniform static magnetic field within the test chamber of the vessel. An RF coil is embedded in the walls of the vessel and is used to induce excitation field with a direction perpendicular to the static magnetic field. Fluids located proximate the borehole are introduced into a test chamber of the tester. NMR signals from the excited nuclei in the fluids are detected to obtain data for calculating a number of important fluid parameters and for the interpretation of wireline MRIL measurements.

40 Claims, 4 Drawing Sheets

U.S. PATENT DOCUMENTS

| | | | |
|---|---|---|---|
| 3,205,477 | 9/1965 | Kalbfell . | |
| 3,213,357 | 10/1965 | Brown et al. . | |
| 3,360,716 | 12/1967 | Bloom et al. . | |
| 3,395,337 | 7/1968 | Varian . | |
| 3,402,344 | 9/1968 | Brown et al. . | |
| 3,453,433 | 7/1969 | Alger et al. | 250/83.33 |
| 3,508,438 | 4/1970 | Alger et al. | 73/152 |
| 3,567,935 | 3/1971 | Nagel | 250/83.1 |
| 3,567,936 | 3/1971 | Tittman | 250/83.1 |
| 3,590,228 | 6/1971 | Burke | 235/151.35 |
| 3,593,116 | 7/1971 | Culpepper | 324/5 |
| 3,617,867 | 11/1971 | Herzog | 324/5 |
| 3,638,484 | 2/1972 | Tixier | 73/152 |
| 3,657,730 | 4/1972 | Robinson et al. | 324/5 |
| 3,667,035 | 5/1972 | Slichter | 324/5 R |
| 3,777,560 | 12/1973 | Guignard | 73/151.5 |
| 3,784,898 | 1/1974 | Darley et al. | 324/5 R |
| 3,896,668 | 7/1975 | Anderson et al. | 73/152 |
| 4,291,271 | 9/1981 | Lauffer | 324/307 |
| 4,310,887 | 1/1982 | Suau | 364/422 |
| 4,528,508 | 7/1985 | Vail, III | 324/303 |
| 4,686,364 | 8/1987 | Herron | 250/256 |
| 4,710,713 | 12/1987 | Taicher et al. | 324/303 |
| 4,717,876 | 1/1988 | Masi et al. | 324/303 |
| 4,717,877 | 1/1988 | Taicher et al. | 324/303 |
| 4,717,878 | 1/1988 | Taicher et al. | 324/303 |
| 4,728,892 | 3/1988 | Vinegar et al. | 324/309 |
| 4,885,540 | 12/1989 | Snoddy et al. | 324/318 |
| 4,933,638 | 6/1990 | Kenyon et al. | 324/303 |
| 4,994,777 | 2/1991 | Leupold et al. | 335/302 |
| 5,023,551 | 6/1991 | Kleinberg et al. | 324/303 |
| 5,055,787 | 10/1991 | Kleinberg et al. | 324/303 |
| 5,055,788 | 10/1991 | Kleinberg et al. | 324/303 |
| 5,122,746 | 6/1992 | King et al. | 324/307 |
| 5,212,447 | 5/1993 | Paltiel | 324/300 |
| 5,280,243 | 1/1994 | Miller | 324/303 |
| 5,309,098 | 5/1994 | Coates et al. | 324/303 |
| 5,349,184 | 9/1994 | Wraight | 250/266 |
| 5,350,925 | 9/1994 | Watson | 250/269.3 |
| 5,363,041 | 11/1994 | Sezginer | 324/303 |
| 5,376,884 | 12/1994 | Sezginer | 324/303 |
| 5,379,216 | 1/1995 | Head | 364/422 |
| 5,381,092 | 1/1995 | Freedman | 324/303 |
| 5,387,865 | 2/1995 | Jerosch-Herold et al. | 324/303 |
| 5,397,989 | 3/1995 | Spraul et al. | 324/321 |
| 5,412,320 | 5/1995 | Coates | 324/303 |
| 5,432,446 | 7/1995 | Macinnis et al. | 324/303 |
| 5,453,692 | 9/1995 | Takahashi et al. | 324/318 |
| 5,486,761 | 1/1996 | Sezginer | 324/303 |
| 5,486,762 | 1/1996 | Freedman et al. | 324/303 |
| 5,497,087 | 3/1996 | Vinegar et al. | 324/303 |
| 5,498,960 | 3/1996 | Vinegar et al. | 324/303 |
| 5,517,115 | 5/1996 | Prammer | 324/303 |
| 5,557,200 | 9/1996 | Coates | 324/303 |
| 5,557,201 | 9/1996 | Kleinberg et al. | 324/303 |
| 5,565,775 | 10/1996 | Stallmach et al. | 324/303 |
| 5,629,623 | 5/1997 | Sezginer et al. | 324/303 |
| 5,680,043 | 10/1997 | Hurlimann et al. | 324/303 |
| 5,705,927 | 1/1998 | Sezginer et al. | 324/303 |
| 5,796,252 | 8/1998 | Kleinberg et al. | 324/303 |

OTHER PUBLICATIONS

Miller et al., "Spin Echo Magnetic Resonance Logging: Porosity and Free Fluid Index Determination,"*Society of Petroleum Engineers* (1990), pp. 321–334.

Kenyon et al., "Pore–Size Distribution and NMR in Microporous Cherty Sandstones," SPWLA Thirtieth Annual Logging Symposium (Jun. 11–14, 1989), pp. 1–24.

Schlumberger Technology News—*Oilfield Bulletin*, "Fifth Generation Nuclear Magnetic Resonance Logging Tool: A Major Advance in Producibility Measurement Technology," (Jul. 1995) (2 pp.).

Akkurt et al. "NMR Logging of Natural Gas Reservoirs," SPWLA 35th Annual Logging Symposium (Jun. 26–29, 1995).

Prammer, M.G., "NMR Pore Size Distributions and Permeability at the Well Site," *Society of Petroleum Engineers* (Sep. 25, 1995) pp. 55–64.

Chandler et al., "Improved Log Quality with a Dual–Frequency Pulsed NMR Tool," *Society of Petroleum Engineers* (1994) pp. 23–35.

Straley et al., "NMR in Partially Saturated Rocks: Laboratory Insights on Free Fluid Index and Comparison with Borehole Logs," SPWLA Annual Logging Symposium (Jun. 27, 1991) pp. 40–56.

Gallegos et al., "A NMR Technique for the Analysis of Pore Structure: Determination of Continuous Pore Size Distributions," Journal of Colloid and Interface Science, vol. 122, No. 1, Mar. 1988, pp. 143–153.

Gallegos et al., "A NMR Technique for the Analysis of Pore Structure: Application to Materials with Well–Defined Pore Structure," Journal of Colloid and Interface Science, vol. 119, No. 1, Sep. 1987, pp. 127–140.

Neuman et al., "Applications of Nuclear Magnetism Logging to Formation Evaluation," Journal of Petroleum Technology, vol. 34, (1982) pp. 2853–2862.

Chandler et al., "Reliable Nuclear Magnetism Logging—With Examples in Effective Porosity and Residual Oil Saturation," SPWLA—28th Annual Logging Symposium, vol. 1, Manuscript C, (1987).

Jackson et al., "Western Gas Sands Project Los Alamos NMR Well Logging Tool Development," Los Alamos National Laboratory (Oct. 1981—Sep. 1982) pp. 1–28.

Clavier et al., "The Theoretical and Experimental Bases for the 'Dual Water' Model for the Interpretation of Shaly Sands," *Journal of Petroleum Technology* (Apr. 1984), pp. 3–15.

Petrakis et al., "The Utilization of Nuclear Magnetic Resonance Spectroscopy for Petroleum, Coal, Oil Shale, Petrochemicals, and Polymers. Phenomenology, Paradigms of Applications, and Instrumentation," 594 Applied Spectroscopy Reviews vol. 15 (1979) No. 2, pp. 195–260.

Brownstein et al., "Importance of classical diffusion in NMR studies of water in biological cells," The American Physical Society, vol. 19, No. 6, (1979) pp. 2446–2453.

Farrar et al., "Pulse and Fourier Transform NMR Introduction to Theory and Methods," Academic Press (1971) pp. 26–29.

Waxman et al., "Electrical Conductivities in Oil–Bearing Shaly Sands," *Society of Petroleum Engineers Journal* (1968) pp. 107–122.

Brown et al., "Nuclear Magnetism Logging," Transactions of the American Institute of Mining, Metallurgical, and Petroleum Engineers, vol. 219 (1960), pp. 199–207.

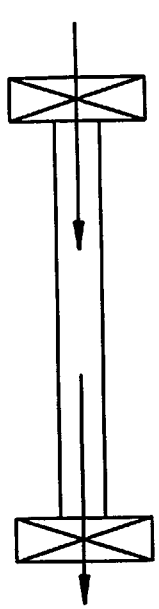 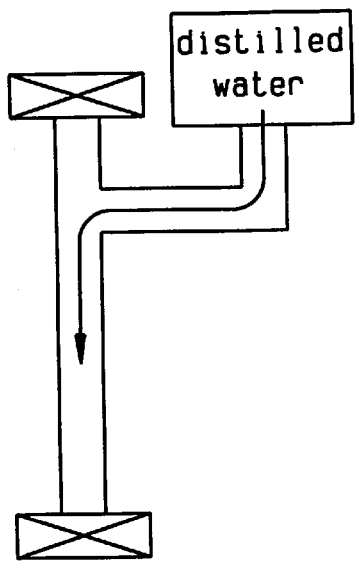 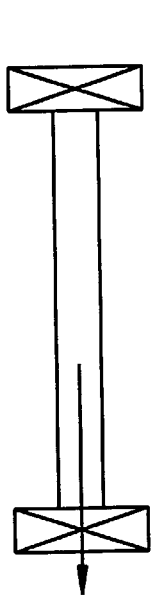 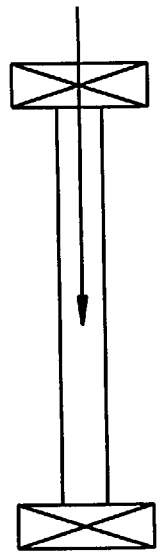
FIG.2A  FIG.2B  FIG.2C  FIG.2D
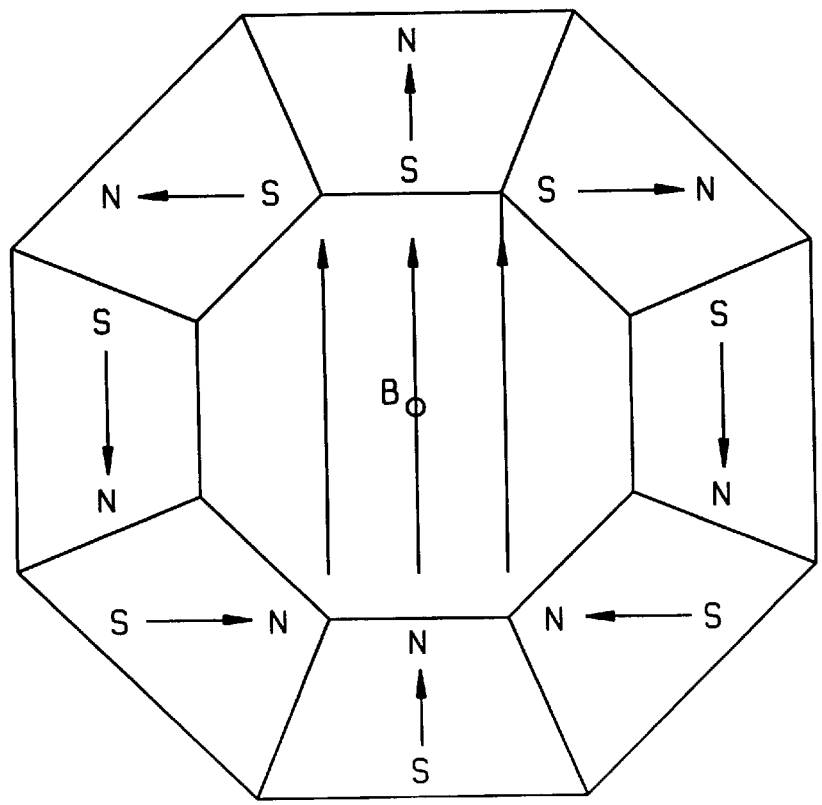
FIG. 3

NUCLEAR MAGNETIC RESONANCE SENSING APPARATUS AND TECHNIQUES FOR DOWNHOLE MEASUREMENTS

FIELD OF THE INVENTION

The present invention relates to borehole measurements and more particularly to downhole measurements of fluids employing nuclear magnetic resonance.

BACKGROUND

Performing measurements on fluid samples is desirable in many oil industry applications. In the prior art such measurements are typically made by bringing samples to the surface using sealed containers, and sending the samples for laboratory measurements. A number of technical and practical imitations are associated with this approach.

The main concern usually is that the sample(s) taken to the surface may not be representative of the downhole geologic formation due to the fact that only limited sample material from a limited number of downhole locations can be extracted and taken to the surface. Thus, taking samples to the surface is impractical if it is desired to measure the fluid on a dense grid of sample points. Therefore, by necessity the measurements will only provide an incomplete picture of the downhole conditions.

In addition, these samples frequently contain highly flammable hydrocarbon mixtures under pressure. Depressurizing the containers frequently leads to the loss of the gas content. Handling of such test samples can be hazardous and costly.

It is therefore apparent that there is a need for direct downhole fluid testing that would overcome these and other problems associated with prior art solutions.

Various methods exist for performing downhole measurements of petrophysical parameters of the geologic formation. Nuclear magnetic resonance (NMR) logging is among the most important methods which have been developed for a rapid determination of such parameters, including formation porosity, composition of the formation fluid, the quantity of movable fluid, permeability and others. At least in part this is due to the fact that NMR measurements are environmentally safe and are unaffected by variations in the matrix mineralogy. In a typical NMR experiment a logging tool is lowered into a drilled borehole to measure properties of the geologic formation near the tool. The tool is pulled up at a known rate and measurements are continuously taken and recorded in a computer memory, so that at the end of the experiment a complete log is generated which shows the properties of the geologic formation along the length of the borehole. Alternatively, NMR logging can be done while the borehole is being drilled.

NMR logging is based on the observation that when an assembly of magnetic moments, such as those of hydrogen nuclei, are exposed to a static magnetic field they tend to align along the direction of the magnetic field, resulting in bulk magnetization. The rate at which equilibrium is established in such bulk magnetization upon provision of a static magnetic field is characterized by the parameter $T_1$, known as the spin-lattice relaxation time. Another related and frequently used NMR logging parameter is the spin-spin relaxation time constant $T_2$ (also known as transverse relaxation time) which is an expression of the relaxation due to non-homogeneities in the local magnetic field over the sensing volume of the logging tool. Both relaxation times provide indirect information about the formation porosity, the composition and quantity of the formation fluid, and others.

Another measurement parameter used in NMR well logging is the formation diffusion. Generally, diffusion refers to the motion of atoms in a gaseous or liquid state due to their thermal energy. Self-diffusion of a fluid is directly related to the viscosity of the fluid, a parameter of considerable importance in borehole surveys. In a uniform magnetic field, diffusion has little effect on the decay rate of the measured NMR echoes. In a gradient magnetic field, however, diffusion causes atoms to move from their original positions to new ones, which also causes these atoms to acquire different phase shifts compared to atoms that did not move. This contributes to a faster rate of relaxation.

It has been observed that the mechanisms which determine the values of $T_1$, $T_2$ and diffusivity depend on the molecular dynamics of the sample being tested. In bulk volume liquids, typically found in large pores of the formation, molecular dynamics is a function of molecular size and inter-molecular interactions which are different for each fluid. Thus, water, gas and different types of oil each have different $T_1$, $T_2$ and diffusivity values. On the other hand, molecular dynamics in a heterogeneous media, such as a porous solid which contains liquid in its pores, differs significantly from the dynamics of the bulk liquid and generally depends on the mechanism of interaction between the liquid and the pores of the solid media. It will thus be appreciated that a correct interpretation of the measurement parameters $T_1$, $T_2$ and diffusivity can provide valuable information relating to the types of fluids involved, the structure of the formation and other well logging parameters of interest.

NMR measurements of geologic formations can be done using, for example, the centralized MRIL® tool made by NUMAR, a Halliburton company, and the sidewall CMR tool made by Schlumberger. The MRIL® tool is described, for example, in U.S. Pat. No. 4,710,713 to Taicher et al. and in various other publications including: "Spin Echo Magnetic Resonance Logging: Porosity and Free Fluid Index Determination," by Miller, Paltiel, Millen, Granot and Bouton, SPE 20561, 65th Annual Technical Conference of the SPE, New Orleans, La., Sept. 23–26, 1990; "Improved Log Quality With a Dual-Frequency Pulsed NMR Tool," by Chandler, Drack, Miller and Prammer, SPE 28365, 69th Annual Technical Conference of the SPE, New Orleans, La., Sep. 25–28, 1994). Details of the structure and the use of the MRIL® tool are also discussed in U.S. Pat. Nos. 4,717,876; 4,717,877; 4,717,878; 5,212,447; 5,280,243; 5,309,098; 5,412,320; 5,517,115 and 5,557,200 all of which are commonly owned by the assignee of the present invention. The Schlumberger CMR tool is described, for example, in U.S. Pat. Nos. 5,055,787 and 5,055,788 to Kleinberg et al. and further in "Novel NMR Apparatus for Investigating an External Sample," by Kleinberg, Sezginer and Griffin, J. Magn. Reson. 97, 466–485, 1992. The content of the above patents are hereby expressly incorporated by reference.

Wireline logging of boreholes performed using the NMR tools described above or other techniques known in the art provides valuable information concerning the petrophysical properties of the formation and in particular regarding the fluid composition of the formation. Additional fluid parameter information can be critical for the interpretation of the wireline NMR measurements. For example, it is often desirable to distinguish between water, connate oil, drilling mud filtrates and gas based on the differences in $T_1$, $T_2$ and diffusivity. The true values for connate oil and the drilling mud filtrates under reservoir conditions are often unknown and must be approximated from laboratory measurements done under different conditions. Therefore, for increased accuracy, it is desirable to perform real-time downhole NMR determination of the $T_1$, $T_2$ and diffusivity parameters of borehole fluids to enhance the quality and reliability of the formation evaluation obtained using the standard measurements.

Direct downhole measurements of certain fluid properties is known in the art. Several commercially available tools can be used to this end. Examples include the RDT tool manufactured by Halliburton, the Reservoir Characterization Instrument (RCI) from Western Atlas, and the Modular Formation Dynamics Tester (MDT) made by Schlumberger. These tester tools have modular design that allows them to be reconfigured at the well site. Typically, these tools provide pressure-volume measurements, which can be used to differentiate liquids from gases, and are also capable of providing temperature, resistivity and other mechanical or electrical measurements. However, none of these tools is presently capable of providing NMR measurements, such as hydrogen density, self diffusivity or relaxation times.

Therefore, there is a need for a tester capable of performing direct downhole NMR measurements that can be used to enhance the quality and reliability of formation evaluation obtained using prior art techniques. Additionally, there is a need to provide a modular NMR downhole tester that can be used as an add-on to existing testing equipment so as to minimize the cost of the extra measurements.

SUMMARY OF THE INVENTION

Accordingly, it is an object of the present invention to provide a method and apparatus using nuclear magnetic resonance (NMR) techniques for obtaining information relating to fluids present near geologic structures. In particular, a modular NMR tester is provided for making direct downhole NMR measurements of various parameters of fluid samples of geologic formations near the walls of a borehole. The modular tester is preferably incorporated as an add-on part to a standard commercial downhole formation tester.

In operation, test fluids located proximate the borehole are introduced into a test chamber of the tester. In a preferred embodiment, the tester comprises a vessel made of a non-conductive material and a surrounding permanent magnet that creates a uniform static magnetic field within the test chamber. In a preferred embodiment, an RF coil is embedded in the walls of the vessel and is used to induce an excitation field with a direction perpendicular to the static magnetic field. NMR signals from the excited nuclei in the fluids are detected to obtain data for directly estimating a number of fluid parameters or to assist in the interpretation of wireline MRIL measurements.

More specifically, in a preferred embodiment, an apparatus is provided for conducting downhole NMR measurements of fluids comprising: a vessel for containing fluids; at least one magnet defining a longitudinal axis and having substantially uniform magnetization and a magnetization direction along an axis perpendicular to the longitudinal axis to generate a static magnetic field in the vessel; and at least one RF coil operative to generate a RF magnetic field in the vessel in a direction substantially perpendicular to the static field direction for exciting nuclei of fluids in the vessel.

The apparatus may further comprise one or more electromagnets operative to generate a variable gradient magnetic field in the vessel in a direction parallel to the static magnetic field, and a receiver for acquiring NMR signals from the excited nuclei and for providing an output indication of the properties of the fluids sought to be analyzed. A reservoir tank containing reference fluid is also provided in a preferred embodiment for calibrating the tester.

In a preferred embodiment, the vessel is fabricated of fiberglass and the RF coil is embedded in the fiberglass walls of the vessel.

The method of the present invention for conducting downhole borehole NMR measurements in a preferred embodiment comprises the steps of: receiving a fluid in a test chamber of a vessel located in the borehole; generating a substantially uniform static magnetic field in the test chamber of the vessel with a defined magnetization direction; generating a radio frequency (RF) magnetic field for exciting nuclei of the fluid in the test chamber, said RF field having a magnetic direction substantially perpendicular to the direction of the static magnetic field; and measuring a set of NMR signals generated from excited nuclei of the fluid to determine properties of the fluid which is being tested.

In another preferred embodiment, the method further comprises the step of generating a variable magnetic field in the vessel in a direction parallel to the direction of the static magnetic field. In this embodiment, the method of the present invention provides measurements of properties of the fluid which comprise: (a) the density of the excited atomic elements; and (b) the nuclear relaxation times $T_1$ and $T_2$ of the excited nuclei in the test fluid; and (c) the self diffusivity of the test fluid.

In addition, in a preferred embodiment the method of the present invention further comprises the step of measuring a set of NMR signals for a calibration fluid to provide a reference set for comparison with NMR signals from test fluids.

In a preferred embodiment, the method of the present invention further comprises, prior to the step of providing the fluid to be tested, the step of providing a NMR log measurement along the borehole to determine target zones for extracting test fluid from the borehole.

BRIEF DESCRIPTION OF THE DRAWINGS

The present invention will be understood and appreciated more fully from the following detailed description taken in conjunction with the drawings in which:

FIGS. 2A through 2D illustrate the steps involved in measuring fluids using the modular NMR testing apparatus of the present invention;

FIG. 3 is an illustration of the configuration of a permanent magnet used in accordance with the present invention to generate a constant uniform magnetic field inside the measurement vessel;

DETAILED DESCRIPTION

Figure 1:
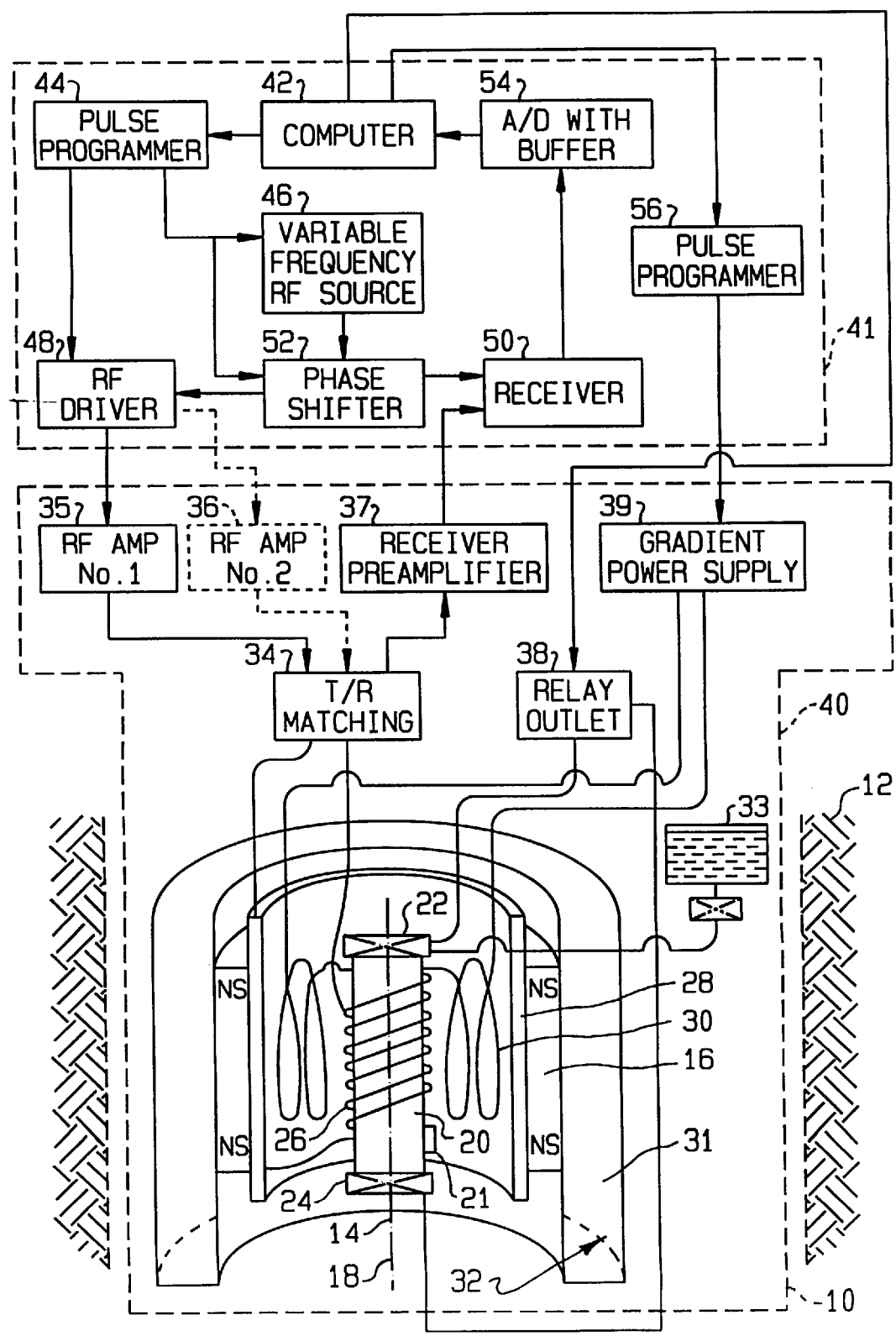
FIG. 1 is a partially pictorial, partially block diagram illustration of a modular fluid testing apparatus in accordance with the present invention for obtaining nuclear magnetic resonance measurements of fluids near a geologic structure.

Reference is now made to FIG. 1, which illustrates in a schematic form a modular downhole NMR fluid tester constructed and operative in accordance with the present invention. It should be emphasized that the tester in accordance with a preferred embodiment is a separate module which is designed to fit into any one of several commercially available modular downhole test tools. As noted before, examples of such test tools include the RDT tool manufactured by Halliburton, the Reservoir Characterization Instrument (RCI) from Western Atlas, and the Modular Formation Dynamics Tester (MDT) made by Schlumberger. The modular design of these tester tools allows them to be reconfigured at the well site to meet a wide variety of testing needs. In accordance with the present invention one such reconfiguration is to include the modular NMR fluid tester described herein as a separate module to obtain downhole NMR measurements of raw fluids simultaneous with or in addition to the standard measurements performed by these tools. It should therefore be understood that FIG. 1 is merely a schematic illustration in which for simplicity none of the external equipment, including the commercial tool, is shown.

With reference to FIG. 1, the test portion 10 of the NMR downhole tester in accordance with the present invention is arranged to be lowered into a borehole 12 having a borehole longitudinal axis 14 in order to examine the nature and the properties of fluids in the vicinity of borehole 12.

In a preferred embodiment, test portion 10 comprises a tubular permanent magnet 16, having a longitudinal axis 18. In the illustrative embodiment shown in FIG. 1 the axis 18 is parallel or coaxial with the longitudinal axis 14 of the borehole but in general its orientation with respect to the borehole is not critical.

The length of the permanent magnet 16 used in the present invention is generally determined by design constraints. In particular, this length affects the signal-to-noise ratio (SNR) of the measured signals with longer magnets resulting in improved SNR. In a specific embodiment illustrated in FIG. 1, a single permanent magnet 16 is used. According to an alternative embodiment of the invention, two or more of permanent magnets 16 may be stacked together to form a longer composite magnet. These magnets will be referred to collectively as permanent magnet 16 and their common longitudinal axis will be identified as longitudinal axis 18. Permanent magnet 16 functions to generate a constant uniform magnetic field $B_0$ which is substantially perpendicular to the longitudinal axis 18.

Located within permanent magnet 16 of the test portion 10 is pressure vessel 20 having a test chamber therein for holding fluid samples. As shown in the figure, pressure vessel 20 has a longitudinal axis which is coaxial with longitudinal axis 18 of the permanent magnet. Pressure vessel 20 is fabricated of non-conductive materials such as ceramics, or preferably fiberglass. Generally, it is required that the material of which the vessel is made be capable of withstanding the temperature and pressure conditions in a typical borehole environment. The dimensions of the vessel are not critical and are determined from design constraints of the logging tool housing the modular NMR tester of the present invention. In a preferred embodiment, the inside diameter of the vessel 20 is approximately 1 cm and the test chamber is approximately 15 cm high, so that the vessel is capable of holding a sample volume of approximately 10 $cm^3$. Different holding volumes may be used, if desired.

Vessel 20 is adapted to receive and discharge fluids and to this end is connected by inlet valve 22 and outlet valve 24 to external pressure tubes (not shown) which form part of the logging tool and are typically made of steel. Valves 22 and 24 are operated to allow fluid samples to enter the instrument from one end, preferably from the top in order to use the force of gravity, hold samples for the duration of the NMR measurements and to discharge samples from the other end after completion of the NMR measurement cycle.

The external equipment required to supply the borehole fluids to be tested to the pressure vessel 20 is generally known in the art and need not be described in much detail. In the simplest case, it comprises a pressure probe that is hydraulically activated from within a module that isolates the borehole pressure from the probe. The probe penetrates the mud in the borehole and is inserted into the rock at a desired location in the sidewall of the borehole. Generally, the invading fluid in the borehole is sealed off, so that preferably only native fluid from the rock is pumped into the tester. In accordance with a preferred embodiment of the present invention, at least a portion of this fluid is diverted through valve 22 into the test chamber of the NMR tester described herein. For a more detailed description of the external equipment the reader is directed to the product literature concerning the commercially available logging tools, such as those manufactured by Halliburton, Schlumberger and Western Atlas.

In alternative embodiments of the present invention (not shown) vessel 20 need not be closed as illustrated in FIG. 1, so that one or both of valves 22 and 24 can be eliminated. Thus, in a specific embodiment vessel 20 is merely a portion of a duct in which fluid to be tested may flow continuously. In such case, measurements are taken on the volume of fluid surrounded by the permanent magnet at the time of the NMR experiment (the test volume). In an alternative embodiment, vessel 20 only has one closed end illustrated in FIG. 1, for example, by valve 24. In this case, the flow of the fluid can be interrupted during measurements by closing off valve 24, and can resume by opening the valve on command by the computer. In each case, provisions can be made to expel fluids from the test volume by various means, as known in the art. Finally, control of the fluid flow may be implemented using the external equipment. It should thus be understood that in the context of the present invention vessel 20 can be either a closed container or a duct or an arrangement that enables controlled flow of fluid through the volume surrounded by the permanent magnet.

In accordance with the present invention test portion 10 of the testing apparatus further comprises one or more coil windings 26 which are arranged around vessel 20. Since it is important to have the coil windings 26 as close to the fluid sample as possible for the NMR measurements performed using this device, in a preferred embodiment windings 26 are embedded in the walls of pressure vessel 20. In operation, coil 26 generates a magnetic field $B_1$ to excite nuclear magnetic relaxation in the test fluid and then receives NMR signals from the fluid samples contained within vessel 20. The magnetic field $B_1$ is polarized in a direction parallel to the longitudinal axis 18 of the permanent magnet 16, and thus is perpendicular to the direction of the magnetic field $B_0$. In a preferred embodiment, the $B_1$ field is operated at a frequency which can be varied in accordance with the strength of the $B_0$ field. As known in the art, the required operating frequency of the magnetic field is given by the expression $F_1=42,580\ B_0$, where 42,580 is the gyromagnetic ratio constant. In a specific illustrative embodiment where $B_0$ is 47 milli Tesla (mT), $B_1$ is operated at approximately 2 MHz. It should be noted that in a preferred embodiment the matching and tuning circuit for the coil 26 enable single-tuning, i.e., for hydrogen frequency only, or multiple-tuning for NMR measurements of additional elements, such as the $^{13}C$ isotope. This feature of the present invention is based on the well-known fact that the same magnetic field produces different operating frequencies for different atomic elements.

With reference to FIG. 1, the return path of the coil current is provided through a copper shield 28 that separates the interior, radio frequency section of test portion 10 from the permanent magnet. Accordingly, the magnetic field lines of $B_1$ do not penetrate the permanent magnet and cannot excite magneto-acoustic oscillations which are undesirable.

In the preferred embodiment illustrated in FIG. 1, a magnetic field gradient coil or plurality of coils 30 is located between coil windings 26 and copper shield 28 to generate a magnetic field gradient. The gradient coil 30 is essential for performing rapid, high-SNR self diffusion measurements. In a preferred embodiment, coil 30 is of a saddle type with two separate loops generating fields in the x direction. In a preferred embodiment, saddle coil 30 is driven as a Maxwell pair such that the gradient field enhances the uniform field $B_0$ in the positive x direction and opposes it in the negative x direction, thereby creating a steerable field gradient $dB_0/dx$.

In accordance with the present invention, permanent magnet 16, pressure vessel 20, coil windings 26 and field gradient coils 30 are preferably housed in a protective housing or pressure barrel 31.

The coil windings 26, together with a (T/R) matching circuit 34 shown in FIG. 1 define a transmitter/receiver (T/R) circuit required for the NMR measurements performed in accordance with the present invention. T/R matching circuit 34 typically includes a resonance capacitor, a T/R switch and both to-transmitter and to-receiver matching circuitry. Circuit 34 is coupled to a first RF power amplifier 35 and optionally a second RF amplifier 36 and to a receiver preamplifier 37. A relay outlet 38 is linked to valves 22 and 24. A power supply 39 provides the dc current required for the magnetic field gradient generating coil(s) 30.

The coil 26 shown in FIG. 1 is of a solenoid type. In an alternative embodiment of the present invention (not shown) coil 26 may be of a saddle type. In this case, with reference to FIG. 1, the windings of the coil would face away from the drawing sheet as to generate a magnetic field with the appropriate direction.

In another embodiment of the present invention (not shown), two separate coils are used—one as a transmitter and the other as a receiver antenna. In such case, in accordance with the present invention one of the coils is of a solenoid type (as shown in FIG. 1) whereas the other is of a saddle type and is positioned as described in the preceding paragraph. In a preferred embodiment of the present invention, the solenoid type coil is used as a receiving antenna and is preferably embedded in the walls of the vessel as to increase its sensitivity. The saddle type coil is used in this case as a transmitter, and is located further away from the axis of the vessel compared with the receiver. Alternatively, the saddle type coil can be used a receiver and the solenoid coil as a transmitter. An advantage of having two antennae in accordance with this embodiment of the present invention is that in such case there is no need for a T/R matching circuit 34, so that the transmitter antenna can be connected directly to RF amplifier 35, whereas the receiver antenna can be connected directly to preamplifier 37.

In accordance with the present invention the calibration of the testing apparatus is accomplished using calibration fluid. As shown in a specific embodiment in FIG. 1, a reservoir tank 33 holding calibration fluid, such as distilled water, can be located proximate the pressure barrel 31. In a preferred embodiment, the water may be doped with cupric sulfate to lower the NMR relaxation times to approximately 200 milliseconds at reservoir temperatures. The vessel 20 can be filled with approximately 10 $cm^3$ fluid at a time from the reservoir tank 32. Since the hydrogen content and the self-diffusion coefficient of distilled water as a function of temperature are known, measurements on the water sample serve as tool calibrations under actual temperature and pressure conditions. The artificially lowered relaxation times, $T_1$ and $T_2$, permit rapid pulsing and therefore fast acquisition of NMR signals. Temperature measurements are made in accordance with the present invention using a transducer 21, as shown in FIG. 1. In alternative embodiments of the present invention, calibration fluid is used to fill the vessel 20 prior to lowering the device in the borehole, so that there is no need for a separate reservoir tank.

In a specific embodiment, all of the elements described above are contained in a housing 40 which in operation forms part, i.e., an add-on, of a larger logging tool and is passed along with the tool through the borehole. In alternative embodiments some of the elements illustrated in FIG. 1 as part of the housing 40 may be located above ground.

Block 41 in FIG. 1 depicts in a block diagram form the control circuitry used in a preferred embodiment of the present invention for the downhole NMR tester. As shown, the control circuitry generally comprises a computer 42 which provides a control output to a pulse programmer 44. Pulse programmer 44 is responsible for generating NMR pulse sequences of predetermined frequency, phase shift and duration. To this end, pulse programmer 44 controls the operation of a variable frequency RF source 46 and phase shifter 52, as well as an RF driver 48. The pulsed RF output of driver 48 which has the appropriate frequency and phase shift is supplied to RF power amplifier 35 and optionally to RF amplifier 36. The output of amplifier 35 (and/or 36) is finally passed through T/R matching circuit 34 to coil 26 which generates the magnetic field $B_1$ to excite nuclei in the fluid being tested.

NMR echo signals generated from the excited nuclei in the fluid contained in the test chamber are picked up by the coil 26 and passed through the T/R matching circuit 34 to receiver pre-amplifier 37. The output of RF receiver preamplifier 37 is supplied to an RF receiver 50 which may receive an input from phase shifter 52. The output of receiver 50 is provided via an A/D converter with a buffer 54 to computer 42 for further processing and analysis of the NMR echo signals. Pulse programmer 56 controls the gradient coil power supply 39 controlling the current flow, and hence the generation of field gradients, according to the commands of the computer 42.

Control circuits for generating pulse sequences having predetermined parameters and for measuring NMR echo signals from test materials and their operation are generally known in the art and need not be described in detail. Therefore, it should be understood that the configuration shown in FIG. 1 is only illustrative and may be varied in alternative embodiments operating in accordance with the principles of the present invention.

Reference is now made to FIGS. 2A through 2D which illustrate certain steps involved in a specific embodiment for measuring fluids using the modular tester of the present invention. Thus, in FIG. 2A, both valves are open and water is flushed through the test chamber of the pressure vessel 20 in preparation for the testing of fluids. Thereafter, both valves are closed and as shown in FIG. 2B, calibration fluid, such as distilled water, is sent to fill vessel 20 for NMR testing and recordation. NMR testing is performed on the calibration fluid in order to provide a point of reference for subsequent fluids to be tested. It will be appreciated that reference points obtained in this measurement are stored in a memory of computer 42. FIG. 2C illustrates the step of discharging the calibration fluid through the open lower valve after the calibration measurements have been taken. At this point, the apparatus is ready for testing of fluids within the borehole. FIG. 2D represents a sample fluid being taken through the open upper valve into vessel 20 for testing.

FIG. 3 illustrates the makeup of a permanent magnet 16 which is used in accordance with a preferred embodiment of the present invention to provide a constant uniform magnetic field $B_0$ in the area of testing. It can be appreciated that the direction of the $B_0$ field is substantially perpendicular to the longitudinal axis 18 of the permanent magnet 16. Preferably, the magnet 16 is constructed from Samarium-Cobalt segments configured as a Halbach magnet to generate a constant uniform field on the inside and little residual field on the outside of the test assembly. The construction of the magnet is disclosed, for example, in U.S. Pat. No. 4,931,760 for use in a medical imaging application. As noted above, the strength of the magnetic field $B_0$ is not critical and can be varied for different designs. In a specific illustrative embodiment $B_0$ is approximately 47 mT. A design using $B_0$=100 mT has also been developed. It should be noted that the magnetic components and field strength used in accordance with the present invention are not limited to the materials and strength mentioned.

The method of the present invention is practiced typically using a two-pass technique. Thus, in a preferred embodiment, the first pass through the borehole can be performed using, for example, the MRIL® tool described above to obtain a fast log providing an indication of the petrophysical properties of the rock in the vicinity of the borehole. Following this stage, the complete log of the rock formation along the borehole can be used in accordance with the present invention to identify target zones of interest for performing direct measurements. The measurements made in the first pass are well known in the art and need not be described in detail. The reader is directed to the disclosures of U.S. Pat. Nos. 4,710,713; 4,717,876; 4,717,877; 4,717,878; 5,212,447; 5,280,243; 5,309,098; 5,412,320; 5,517,115 and 5,557,200 all of which are commonly owned by the assignee of the present invention. Additional information is provided in U.S. Pat. Nos. 5,055,787 and 5,055,788. The content of these patents is hereby expressly incorporated by reference for all purposes.

Once the target zones have been identified, a second pass is made in accordance with a preferred embodiment of the present invention using any one of the commercial downhole testers described above. Second pass measurements are typically made only in the target zones as a cost saving measure. The direct downhole NMR measurements using the modular tester of the present invention are performed next as described below. Finally, the results of the NMR measurements are interpreted directly, and/or used to provide more accurate interpretation of the log obtained in the first pass.

In an alternative embodiment, provisions can be made for using the modular NMR tester of the present invention to perform measurements during the drilling of the borehole, or as part of the first pass described above.

In accordance with the present invention, the downhole NMR tester is used to provide measurements of one or more of the following parameters of the fluid samples: (a) hydrogen density, i.e., the number of hydrogen atoms per unit volume; (b) self-diffusivity (which is inversely related to the fluid viscosity); and (c) nuclear relaxation times $T_1$ and $T_2$ for different operating frequencies depending on the atomic elements of interest. Additional measurements can be made using the multiple-tuning capability of the tester for estimating, for example, carbon density, hydrogen-carbon coupling and/or obtaining polarization transfer information, and others.

Figure 4:
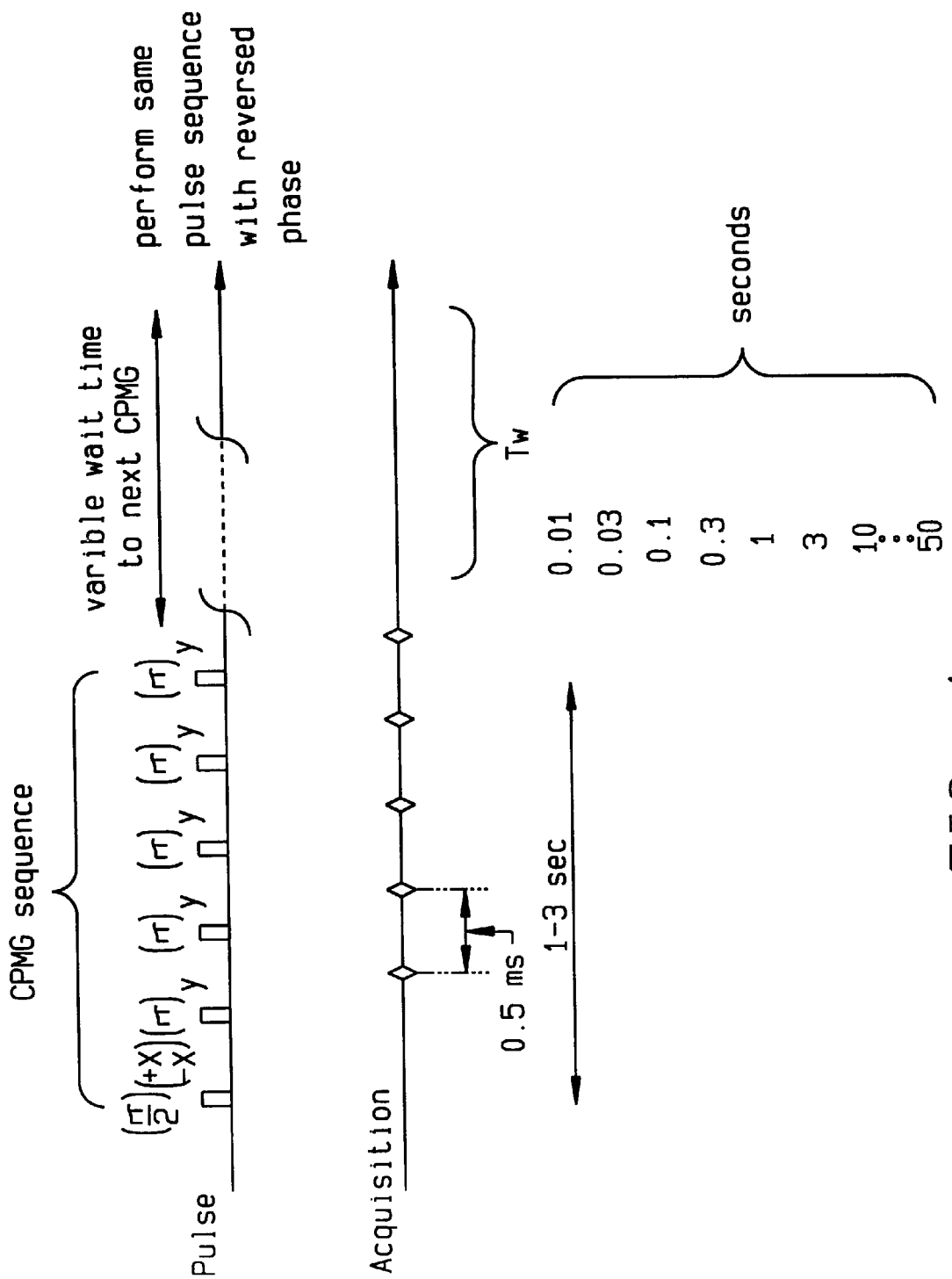
FIG. 4 is a graphical illustration of a pulse and echo acquisition sequence used for NMR fluid measurements in accordance with a preferred embodiment of the present invention.

In accordance with a preferred embodiment of the present invention, the determination of the hydrogen index, and the $T_1$ and $T_2$ relaxation times is based on CPMG pulse-echo trains having an echo spacing of approximately 0.5 milliseconds (ms) as shown in FIG. 4. Approximately 10,000 pulse signals can be generated and the corresponding echo signals can be digitized, stored and accumulated in a specific embodiment. The methods for parameter derivation using such NMR measurements are known in the art and need not be discussed in detail. In the specific application, however, it is necessary to determine certain operating parameters of the system.

For example, the echo acquisition time in a preferred embodiment is approximately 0.1 ms. Other times can also be used, if desired. Assuming an echo acquisition time of 0.1 ms, the maximum tolerable field distortion is then determined using the condition $T_2^* \gg 0.1$ ms, where $T_2^*$ is a time constant which characterizes the apparent NMR signal decay. By setting a lower limit for $T_2^*$ of 0.5 milliseconds, r.m.s. field distortions equivalent to 2 kHz or 0.1% of the main $B_0$ field are allowed.

It is important to realize that relaxation times of bulk fluids can be as high as 10 sec in reservoir conditions. To achieve an error of less than about 1% the hydrogen index, measurements must be spaced out to about five times the relaxation times, i.e., to about 50 sec. Therefore, it would clearly be impractical to perform a large number of individual measurements in order to increase the signal SNR and only a few measurements must suffice to achieve the required signal SNR. In this regard, it is worth emphasizing that in accordance with a preferred embodiment of the present invention the SNR of the measured signals can be varied simply by changing the measurement volume of fluid in the test chamber. As noted above, this can be accomplished in the tester of the present invention by expanding the chamber along its longitudinal axis, and correspondingly increasing the length of the permanent magnet. It has been estimated that for the illustrative embodiment discussed above wherein the test chamber contains 10 cm$^3$ of fluid, the single measurement SNR is approximately about 100:1.

In accordance with the present invention, the wait time between CPMG pulse-echo trains is determined both by the longest $T_1$ measurements and by the requirements of the $T_1$ measurements. In a preferred embodiment, the wait times used by the tester can be set to 0.01. 0.03, 0.1, 0.3, 1.0, 3.0, 10.0 and 50.0 seconds, as shown in FIG. 4. Other wait time sequences can be used, if desired.

As known in the art, the hydrogen index of the fluid sample is determined by extrapolating the echo amplitudes from at least one phase-alternated CPMG pair to time equal to 0 ($\pi/2$ pulse). The ratio of this amplitude, compared to the amplitude given by the water reference, equals the relative hydrogen content of the sample fluid. It can be appreciated that by using the multi-tuning capability of the tester in accordance with the present invention additional measurements can be made for the presence of other atomic elements, such as $^{13}C$.

The $T_2$ relaxation parameter is determined in accordance with a preferred embodiment of the present invention by transforming the time-domain echo data into a $T_2$ time distribution. The $T_1$ relaxation time is determined in a preferred embodiment of the present invention by observing the effect of different wait times on the time equal to 0 ($\pi/2$ pulse) amplitude. The resultant recovery curve can be transformed into a $T_1$ time distribution, as known in the art.

Figure 5:
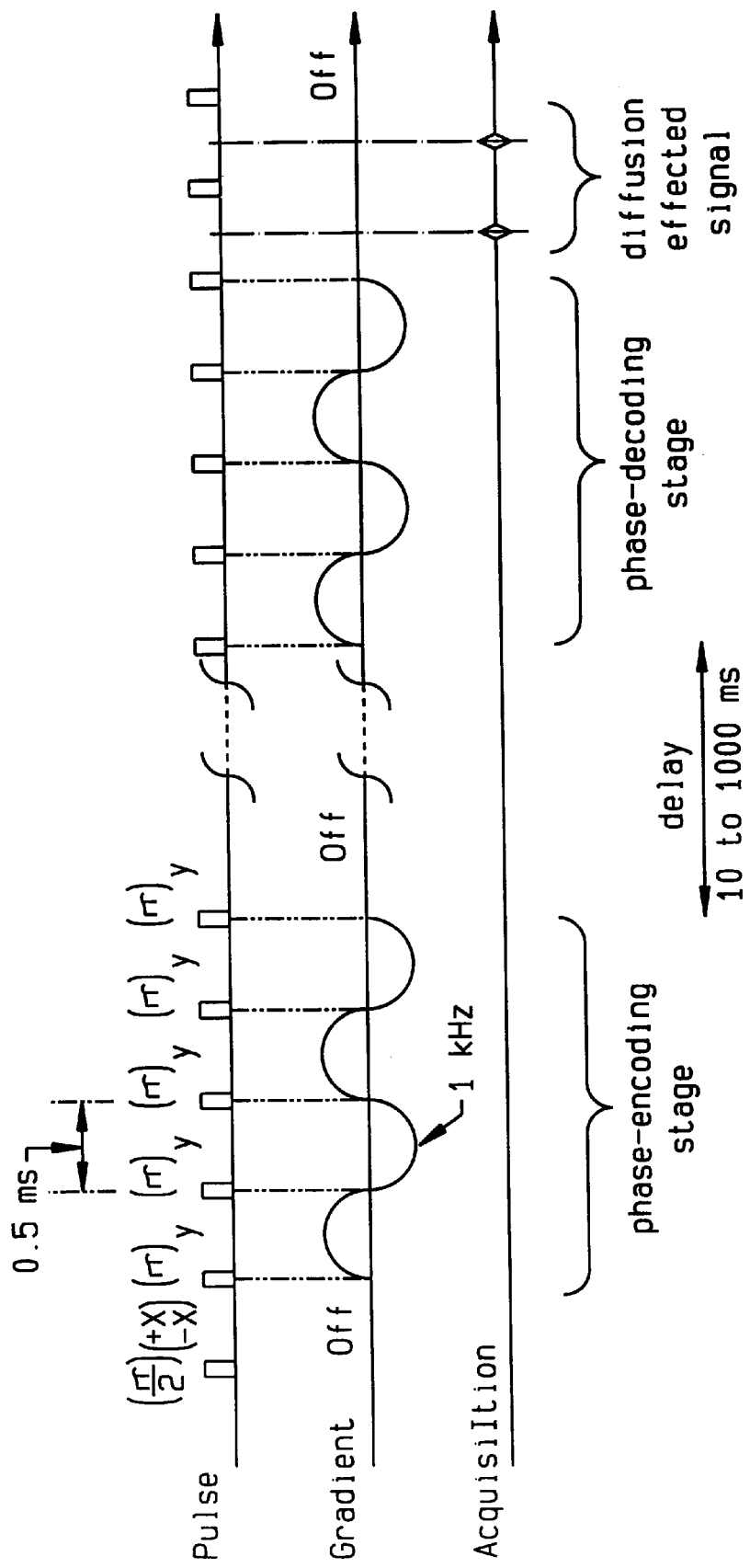
FIG. 5 is a graphical illustration of a pulse sequence and a corresponding time function of the gradient field used for diffusion measurements in accordance with a preferred embodiment of the present invention.

In accordance with the present invention, the downhole NMR tester can further be used to provide diffusivity and viscosity measurements. Referring to FIG. 5, a field gradient is used in a preferred embodiment to perform these measurements. In particular, the field is used to overcome the background field variations using the following steps.

As shown in FIG. 5, a standard CPMG sequence is used with an echo spacing of about 0.5 milliseconds. This short echo spacing greatly attenuates the effects of the gradients arising from an imperfect magnetic field $B_0$. The actual echo spacing can be varied within some limits. In the beginning of the CPMG train, the gradient is turned on with a frequency corresponding to the selected echo spacing time for a few cycles. In the specific embodiment using 0.5 ms echo spacing, a gradient frequency of 1 kHz is used. The amplitude of the gradient field is relatively small compared with the static field and in a preferred embodiment is between a fraction of 1% to about a few percent of the strength of the $B_0$ field. As shown in FIG. 5, the gradient is phase-locked such that its zero-crossings coincide with the pulses being applied. In accordance with the present invention, this period is the phase-encoding stage. Next, the gradient is turned off for an evolution time of about 10 to 1000 ms. In a preferred embodiment, about 100 milliseconds evolution time is used during which time the hydrogen spins are free to diffuse within the measurement volume. After the evolution time, the gradient is turned on again at the select frequency, i.e., 1 kHz, but in a phase that undoes the effect of the phase-encoding stage. After this phase-decoding operation, CPMG echoes are acquired in the usual manner.

It can be appreciated that in the absence of diffusion (corresponding to high viscosity), the final signal is unaffected. Under diffusion, however, the signal attenuation is directly related to the rate of diffusion during the evolution time interval. Accordingly, the measurements of the downhole NMR tester of the present invention can be used to estimate the self-diffusivity and thus the viscosity of the fluid directly.

In essence, the phase-encoding stage used in accordance with the present invention translates the position of the spins into a phase relationship. The phase-decoding stage does the same translation with a negative sign. If there has been a net change in the spin position between the encoding and the decoding stages, the result of applying the two stages will be a net change in the phase relationships that would lead to a reduction of the measured signal amplitude. Accordingly, it can be appreciated that the difference between measurements of the formation fluid with and without the encoding/decoding processing stages can be used to quantify diffusion in the fluid.

In accordance with a specific embodiment of the present invention, the time delay between the phase-encoding and the phase-decoding stages can be varied in some systematic fashion, i.e., 10, 100 and 1000 ms, and changes in the signal amplitudes obtained in each measurement can be used to determine the self-diffusion coefficient of the fluid, as known in the art. In accordance with another embodiment of the present invention, a single strong pulse can be used in the encoding stage and another strong pulse with reverse polarity can be used in the decoding stage of the method.

It will be appreciated by those skilled in the art that the downhole NMR tester and the parameter measurements of the present invention can be used in a number of different ways. For example, as noted above, the measurements can be use to enhance the interpretation of previously conducted log measurements of the borehole by supplying, essentially in real time, true values for connate oil and drilling mud filtrates under reservoir, i.e., raw conditions.

Further, those familiar with the operation of the commercial tester tools will appreciate that measurements can be extended in time, so as to provide a record of the fluid passing through the tester over a predetermined period. For example, as known, the sample probes inserted into the rock can pump fluid out of the rock for periods of about 5–10 minutes to 40 hours in some cases. Assuming that a single downhole NMR measurement takes about 1 minute to complete, in one hour the tester of the present invention can provide 60 independent measurements which are immediately available to the operator. By contrast, a single prior art NMR measurement of a sample taken to the surface may take days to complete. It will be appreciated that to preserve the accuracy of the measurement the test chamber of the vessel 20 can be flushed between measurements, as shown in FIG. 2A. Re-calibration of the tool may be performed in accordance with a pre-determined schedule, for example every two hours.

Although the present invention has been described in connection with the preferred embodiments, it is not intended to be limited to the specific form set forth herein, but on the contrary, it is intended to cover such modifications, alternatives, and equivalents as can be reasonably included within the spirit and scope of the invention as defined by the following claims.

What is claimed is:

1. An apparatus for conducting downhole nuclear magnetic resonance (NMR) measurements of formation fluids comprising:

a vessel adapted to withstand borehole environment conditions for containing formation fluids and for conducting downhole NMR measurements;

at least one magnet defining a longitudinal axis and having substantially uniform magnetization and a magnetization direction along an axis perpendicular to the longitudinal axis to generate a static magnetic field in the vessel; and at least one radio frequency (RF) coil operative to generate series of pulsed RF magnetic fields in the vessel in a direction substantially perpendicular to the static field direction for exciting nuclei of fluids contained in the vessel, and at least one RF coil operative to receive NMR spin echo signals.

2. The apparatus of claim 1 further comprising at least one electromagnet operative to generate a variable gradient magnetic field in the vessel in a direction parallel to the static magnetic field.

3. The apparatus of claim 2 wherein the electro-magnet is located proximate the RF coil and the magnet surrounds the electromagnet, the vessel and the RF coil thereon.

4. The apparatus of claim 3 wherein an electromagnetic shield is located between the magnet and the electro-magnet.

5. The apparatus of claim 4 further including a pressure barrel that contains the vessel, magnet, electro-magnet, RF coil and electromagnetic shield.

6. The apparatus of claim 1 further comprising a receiver for acquiring NMR signals from the excited nuclei and for providing an output indication of the properties of the fluids sought to be analyzed.

7. The apparatus of claim 1 further comprising a reservoir tank for containing a reference fluid.

8. The apparatus of claim 1 wherein said at least one magnet is a permanent magnet.

9. The apparatus of claim 1 wherein the vessel is fabricated of a non-conductive material.

10. The apparatus of claim 9 wherein the vessel is fabricated of fiberglass.

11. The apparatus of claim 9 wherein the coil is embedded in the walls of the vessel.

12. The apparatus of claim 1 wherein said at least one magnet is a Halbach magnet generating uniform static magnetic field $B_0$.

13. The apparatus of claim 12 wherein the uniform magnetic field $B_0$ is approximately 10 to 1000 mT.

14. The apparatus of claim 13 wherein the uniform magnetic field $B_0$ is approximately 100 mT.

15. The apparatus of claim 1 further comprising means for withdrawing fluid from the formation, said means in fluid communication with the vessel.

16. The apparatus of claim 1 wherein NMR measurements of the formation fluid are conducted at formation temperature and pressure conditions.

17. The apparatus of claim 1 wherein said at least one generating and said at least one receiving RF coil are the same.

18. The apparatus of claim 17 wherein said least one generating and said at least one receiving RF coil are of solenoid type.

19. The apparatus of claim 1 wherein said at least one generating and said at least one receiving RF coil are different.

20. The apparatus of claim 19 wherein one of said RF coils is of solenoid type and the other of said RF coils is of a saddle type.

21. The apparatus of claim 1 wherein said series of pulsed RF magnetic fields is a CPMG pulse train.

22. The apparatus of claim 1 wherein an electromagnetic shield is located such that the at least one magnet is on one side of the shield, and said at least one generating and said at least one receiving coils are on the other side of the shield.

23. The apparatus of claim 22 further including a pressure barrel that contains the vessel, the at least one magnet, said at least one generating and said at least one receiving coils RF coil and the electromagnetic shield.

24. A tester module for use with modular downhole formation testers for downhole nuclear magnetic resonance (NMR) testing of formation fluids comprising:

a vessel adapted to withstand borehole environment conditions for containing formation fluids and for conducting downhole NMR measurements;

at least one magnet defining a longitudinal axis and having substantially uniform magnetization and a magnetization direction along an axis perpendicular to the longitudinal axis to generate a static magnetic field in the vessel;

at least one radio frequency (RF) coil operative to generate series of pulsed RF magnetic fields in the vessel in a direction substantially perpendicular to the static field direction for exciting nuclei of fluids in the vessel; and a receiver for acquiring NMR spin echo signals from the excited nuclei and for providing an output indication of the properties of the fluids sought to be analyzed.

25. The tester module of claim 24 further comprising at least one electromagnet operative to generate a variable gradient magnetic field in the vessel in a direction parallel to the static magnetic field.

26. The tester module of claim 25 wherein the vessel is made of non-conductive material and the RF coil is embedded in the vessel, the electro-magnet is located proximate the RF coil and the magnet surrounds the electromagnet, the vessel and the RF coil thereon.

27. The tester module of claim 24 further comprising a reservoir tank for containing a reference fluid.

28. The tester module of claim 24 wherein the uniform magnetic field generated by said at least one magnet is between approximately 10 and 1000 mT.

29. The tester module of claim 24 wherein NMR testing of the formation fluid is conducted at formation temperature and pressure conditions.

30. The tester module of claim 24 wherein said series of pulsed RF magnetic fields is a CPMG pulse train.

31. A method for conducting downhole borehole nuclear magnetic resonance (NMR) measurements of formation fluids comprising the steps of:

receiving a formation fluid in a vessel located in the borehole;

generating a substantially uniform static magnetic field in the vessel with a defined magnetization direction;

generating a series of pulsed radio frequency (RF) magnetic fields for exciting nuclei of the fluid in the vessel, said RF fields having a magnetic direction substantially perpendicular to the direction of the static magnetic field; and receiving NMR spin echo signals generated from excited nuclei of the fluid to determine properties of the fluid.

32. The method of claim 31 wherein said properties of the fluid include one or more of the following: (a) the density of the excited atomic elements; and (b) the nuclear relaxation times $T_1$ and $T_2$ of the excited nuclei in the test fluid.

33. The method of claim 31 further comprising the step of generating a variable magnetic field in the vessel in a direction parallel to the direction of the static magnetic field.

34. The method of claim 31 wherein said properties of the fluid include one or more of the following: (a) the density of the excited atomic elements; and (b) the nuclear relaxation times $T_1$ and $T_2$ of the excited nuclei in the test fluid; and (c) the self diffusivity of the test fluid.

35. The method of claim 31 further comprising the step of receiving asset of NMR spin echo signals for a calibration fluid to provide a reference set for comparison with NMR spin echo signals from other fluids.

36. The method of claim 31 further comprising, prior to the step of receiving a fluid, the step of providing a NMR log measurement along the borehole to determine target zones for extracting fluid from the borehole.

37. The method of claim 36 further comprising the step of utilizing measured parameters of the fluid in combination with the NMR log measurement to enhance the interpretation of the NMR log measurement.

38. The method of claim 31 wherein the steps of:

receiving a fluid; generating a substantially uniform static magnetic field; generating a radio frequency (RF) magnetic field; and measuring a set of NMR signals generated from excited nuclei are repeated for a predetermined set of fluid samples.

39. The method of claim 31 wherein the step of generating a series of pulsed RF magnetic fields comprises generating CPMG pulse trains.

40. The method of claim 35 wherein the step of receiving a set of NMR spin echo signals for a calibration fluid precedes the step of receiving spin echo signals from other fluids.

* * * * *